United States Patent [19]

Sackmann et al.

[11] Patent Number: 5,635,569
[45] Date of Patent: Jun. 3, 1997

[54] SUPERABSORBENT POLYMERS FROM CROSS-LINKED POLYACRYLONITRILE EMULSIONS

[75] Inventors: Günter Sackmann, Leverkusen; Siegfried Korte, Odenthal; Sergej Schapowalow, Leverkusen; Klaus Szablikowski, Walsrode; Wolfgang Koch, Bomlitz, all of Germany

[73] Assignee: Bayer Aktiengesellschaft, Leverkusen, Germany

[21] Appl. No.: 512,835

[22] Filed: Aug. 9, 1995

[30] Foreign Application Priority Data

Aug. 18, 1994 [DE] Germany .................. 44 29 318.6

[51] Int. Cl.$^6$ ........................................ C08F 8/12
[52] U.S. Cl. .............. 525/367; 525/329.1; 525/329.2; 525/329.3; 525/369
[58] Field of Search ........................ 525/367, 369

[56] References Cited

U.S. PATENT DOCUMENTS 3,929,740 12/1975 Engelhardt et al. .
4,357,437 11/1982 Huhn et al. .
5,175,193 12/1992 Heller et al. .
5,356,985 10/1994 Sackmann et al. .

FOREIGN PATENT DOCUMENTS

| 047 381 | 3/1982 | European Pat. Off. . |
| 170 081 | 2/1986 | European Pat. Off. . |
| 241 885 | 10/1987 | European Pat. Off. . |
| 406 648 | 1/1991 | European Pat. Off. . |
| 670 335 | 9/1995 | European Pat. Off. . |
| 1104567 | 2/1968 | United Kingdom . |

*Primary Examiner*—Bernard Lipman
*Attorney, Agent, or Firm*—Connolly and Hutz

[57] ABSTRACT

Superabsorbent polymers based on partly hydrolysed homopolymers and/or copolymers of acrylonitrile which are cross-linked through the incorporation of polyfunctional monomers, wherein 30 to 80 mol-% of the nitrile groups are converted into carboxylate groups, 20 to 70 mol-% of the nitrile groups are converted into carbonamide groups and 0 mol-% to 20 mol-% of the nitrile groups are unchanged, and the said cross-linked polymers possess a swelling capacity of 700 g/g in water and of up to 60 g/g in physiological saline and a gel strength of from 20 g to 100 g, their preparation and their use.

10 Claims, No Drawings

SUPERABSORBENT POLYMERS FROM CROSS-LINKED POLYACRYLONITRILE EMULSIONS

The invention relates to the preparation of superabsorbent polymers in powder form having an extremely high swelling capacity and excellent gel strengths.

Superabsorbent polymers are known and are used mainly in the production of diapers and incontinence articles, but also as materials for water storage in agriculture as well as in the sheathing of electric cables. These superabsorbent polymers are as a rule coarse-meshed cross-linked polymers, insoluble in water and based on alkali salts of polyacrylic acid or copolymers of alkali salts of acrylic acid and acrylamide, which are obtained by radically initiated copolymerisation of acrylic acid and polyfunctional monomers such as divinylbenzene, ethylene glycol dimethacrylate, ethylene glycol diallyl ether, butanediol acrylate, hexanediol methacrylate, polyglycol diacrylate, trimethylolpropane diacrylate, trimethylolpropane trisacrylate, allyl acrylate, diallyl acrylamide, triallylamine, diallyl ether, methylenebisacrylamide and N-methylolacrylamide. By virtue of their structure, these polymers are capable of taking up large quantities of liquids, with associated swelling and the formation of hydrogels, and also of holding these liquids under pressure.

There also exist superabsorbent polymers which are based on hydrolysates of graft copolymers of acrylonitrile on starch as well as those based on cross-linked starch-acrylic acid graft copolymers wherein the carboxyl groups are partly neutralised.

The acidic or alkaline hydrolysis of polyacrylonitrile also leads to polymers having carboxyl or carboxylate groups.

The latter are as a rule soluble in water (and therefore not capable of swelling) because the polyacrylonitrile used as starting material and obtained by precipitation polymerisation has too low a molecular weight.

According to the invention superabsorbent polymers having a high swelling (water-retention) capacity and excellent gel strength can also be prepared from cross-linked aqueous acrylonitrile polymer emulsions.

The invention therefore provides a method for the preparation of cross-linked superabsorbent polymers having a swelling capacity for aqueous liquids of up to 700 g/g and for electrolyte solutions of up to 60 g/g and gel strengths of from 20 to 100 g, whereby aqueous emulsions of sparsely to moderately cross-linked homopolymers and/or copolymers of acrylonitrile are partly hydrolysed by reaction with aqueous solutions of alkali hydroxides, the polymers are precipitated as powders by addition of organic solvents which are miscible with water, are separated out, dried and then optionally heated for a short period.

It is known from the German Patent Application P 42 33 026.2 that highly concentrated aqueous emulsions of homopolymers and copolymers of acrylonitrile having average particle diameters of from 100 to 300 nm can be prepared with the aid of particular anionic polymeric emulsifiers. If a mixture of from 96.0 to 99.8% by weight of acrylonitrile and from 4.0 to 0.2% by weight of a polyfunctional monomer is now introduced during the preparation of these emulsions, fine-particled emulsions having particle sizes of between 100 and 300 nm are likewise obtained. The acrylonitrile polymers formed in this case are cross-linked and, after precipitation from the emulsion, can no longer be dissolved in the solvents suitable for polyacrylonitrile such as, for example, DMF or DMAc. If these aqueous acrylonitrile polymer emulsions are treated with aqueous solutions of alkali hydroxides, then within a short period a partial conversion of the nitrile groups to carboxylate and carbonamide groups takes place at 50° to 100° C., preferably at 70° to 95° C. After working up the product, cross-linked insoluble powders are obtained which swell considerably in water, in electrolyte solutions and in blood, and have extremely favourable superabsorbent properties.

The invention also provides superabsorbent polymers based on partly hydrolysed homopolymers and/or copolymers of acrylonitrile which are cross-linked through the incorporation of polyfunctional monomers, in which polymers 30 to 80 mol-% of the nitrile groups are converted into carboxylate groups, 20 to 70 mol-% of the nitrile groups are converted into carbonamide groups and 0 to 20 mol-% of the nitrile groups are unchanged, with the said cross-linked polymers possessing a swelling capacity of up to 700 g/g in water and of up to 60 g/g in physiological saline and gel strengths of from 20 to 100 g.

Preferred superabsorbent polymers are those wherein 30 to 50 mol-% of the nitrile groups are converted into carboxylate groups and 20 to 40 mol-% of the nitrile groups are converted into carbonamide groups, while 5 to 20 mol-% are unchanged.

The preparation of aqueous emulsions of high molecular homopolymers or copolymers of acrylonitrile, which polymers are not cross-linked, is described in the German Patent Specification P 42 33 026.2. The starting materials for the preparation of the superabsorbent polymers according to the present invention can be obtained by this method, which is carried out in the presence of a polymeric anionic emulsifier and leads to fine-particled (average particle diameter: 100 to 300 nm, determined by laser correlation spectroscopy) polymer emulsions having very high molecular weights. Their average molecular weights (weight average, determined by gel permeation chromatography) are from $5.10^5$ g/mol to $1.10^7$ g/mol, preferably from $2.10^6$ g/mol to $5.10^6$ g/mol.

Cross-linked, insoluble homopolymers or copolymers having particle sizes of between 100 and 300 nm can also be prepared by the identical method if between 0.2 and 4.0% by weight of polyfunctional monomers such as, for example, divinylbenzene, ethylene glycol dimethacrylate, ethylene glycol diallyl ether, butanediol acrylate, hexanediol methacrylate, polyethylene glycol dimethacrylate, trimethylolpropane trisacrylate, allyl acrylate, diallyl acrylamide, triallylamine, diallyl ether, or methylenebisacrylamide are added to the starting monomer or monomers. After they have been precipitated from the emulsion, the said products are insoluble in solvents such as, for example, DMF or DMAc, which are suitable for dissolving polyacrylonitrile. The degree of cross-linking of the polymers obtained in this way depends on the quantity of polyfunctional monomer used and it may range from being very coarse-meshed to very fine-meshed.

The polymer dispersions obtained by way of example by this method can be reacted directly with the alkali hydroxides; very short reaction times are possible, owing to the small particle sizes and the consequently large surface areas of the polymer particles.

Aqueous, preferably from 0.5 to 10% by weight solutions of alkali hydroxides, for example, NaOH or KOH, can be used for the reaction (hydrolysis). The molar ratio of the nitrile groups of the starting polymers to the hydroxyl groups of the alkali hydroxides is preferably 1:0.9 to 1:0.1, particularly preferably 1:0.7 to 1:0.3. Products having particularly favourable properties in industrial use are obtained when this ratio is from 1:0.5 to 1:0.4. The hydrolysis is carried out as a rule at 50° to 100° C., preferably at 70° to 95° C. The extent of neutralisation of the carboxyl groups formed during the hydrolysis reaction can be altered by adding appropriate quantities of mineral acids such as, for example, HCl. Thus in most cases between 30 and 100%, preferably between 50 and 70% of the carboxyl groups in the end product are neutralised, while the remaining carboxyl groups are present in the acid form.

The reaction time required depends on the reaction temperature and the desired degree of hydrolysis (the latter is, of course, also a function of the reaction temperature). As a rule, 20 to 90 mol-% of the acrylonitrile radicals in the cross-linked acrylonitrile homopolymers or copolymers are converted into carboxylate or carbonamide groups. The properties of the cross-linked superabsorbent polymers can be influenced by the degree of hydrolysis. Thus, for a given degree of cross-linking, the maximal achievable degree of swelling increases with the content of carboxylate groups. But the gel strength of the swelled powders is crucial to the quality of the cross-linked superabsorbent polymers, and the gel strength is determined by the degree of cross-linking. The gel strength of the products increases with an increasing degree of cross-linking, while the maximal degree of swelling decreases. In order, therefore, to obtain products having an optimal set of properties for a particular field of application, a particular degree of cross-linking of the polyacrylonitrile emulsion must be established through the quantity of polyfunctional monomers in the initial monomer mixture, and during the subsequent hydrolysis the reaction temperature, the reaction time and the molar ratio of nitrile groups to hydroxyl groups must be selected through trial and error in such a way that the desired degree of hydrolysis is obtained.

To separate the cross-linked superabsorbent polymers in powder form, after conclusion of the hydrolysis, organic solvents which are miscible with water such as, for example, acetone, methanol or ethanol, are added with vigorous stirring in a quantity which can be up to three times the volume of the aqueous reaction mixture. Preferably ethanol in a volume ratio of 1:1 is used. The superabsorbent polymers are thereby precipitated out as fine-particled, easily filtered powders. After the powders have been dried at 50° to 100° C., they can be graded according to their particle sizes by screening. The particle sizes (average diameter) are between 50 and 3,000 μm. The properties of the superabsorbent polymers, for example, their swelling index, their capacity to retain water and their gel strength, are also dependent on the particle size. The smaller the particles, the more rapidly is the equilibrium swelling state attained.

By subsequently heating the cross-linked superabsorbent polymers to from 150° to 250° C., preferably to from 170° to 210° C., for 2 to 30 minutes, preferably for 5 to 15 minutes, their excellent properties in industrial use can be distinctly improved still further. This relates particularly to the swelling kinetics, that is, the rate of absorption of water and other liquids, the gel strength of the swelled polymers and their capacity to take up aqueous liquids under pressure.

The swelling capacity of the cross-linked superabsorbent materials according to the invention is up to 700 g/g in pure water and up to 60 g/g in physiological saline (0.9%).

The gel strengths of superabsorbent powders swelled with water or with 0.9% saline is, depending on the respective degree of cross-linking, between 20 and 100 g (measured using the Texture Analyzer from the firm Stevens).

The superabsorbent polymers are especially suitable for use in the preparation of articles of hygiene such as, for example, babies' diapers or incontinence articles as well as for the sheathing of electric cables. The products can also be used in agriculture as materials for water storage.

EXAMPLES

EXAMPLE 1

Preparation of a cross-linked polyacrylonitrile emulsion 49.8 g of a 20.1% by weight aqueous solution of an anionic polymeric emulsifier containing sulphonic acid groups and based on an alternating copolymer composed of maleic anhydride and diisobutylene (for details, see DE-OS 38 07 097, Example 2) together with 250 g of deionised water are placed in a 2 liter three-necked flask equipped with a stirrer, reflux condenser, inlet tube for nitrogen and three dropping funnels. The reaction mixture is heated to 60° C., with stirring and with nitrogen being passed over, and the solutions I to III are simultaneously charged over a period of three hours.

| Solution I: | 198.000 g of acrylonitrile |
| | 2.000 g of divinylbenzene |
| Solution II: | 0.358 g of hydrogen peroxide (35% aqueous solution) |
| | 100.000 g of deionised water |
| Solution III: | 0.203 g of hydroxymethanesulphinic acid, Na salt |
| | 100.000 g of deionised water |

When charging is complete, stirring is continued for 6 hours at 60° C. The remaining monomers are then removed by vacuum distillation. After filtration through a 100 μm filter cloth, a fine-particled emulsion having a solids content of 28.4% by weight is obtained.

Average particle diameter: 165 nm (determined by laser correlation spectroscopy)

Preparation of the superabsorbent polymers 186.6 g of the cross-linked polyacrylonitrile emulsion prepared in Example 1, 92.4 g of deionised water and 200 g of a 10% by weight solution of sodium hydroxide are placed, with stirring, in a 2 liter four-necked flask equipped with a reflux condenser, thermometer, dropping funnel and stirrer. The reaction mixture is heated to 95° C. with stirring and with nitrogen being passed over. During heating, the colour of the polymer changes from colourless through yellow to dark red, finally becoming colourless again. After a degree of hydrolysis of 20 to 50% established by quantitative determination of the ammonia escaping—has been achieved, the reaction mixture obtained is cooled to 30° to 40° C. and the unspent sodium hydroxide solution is neutralised by slowly adding hydrochloric acid (within 30 to 60 minutes).

The cross-linked superabsorbent polymer is precipitated by addition of ethanol in portions at 25° to 30° C. with vigorous stirring. The ratio by volume of ethanol to water is 1:1. After filtering the product off and drying it in a vacuum drying cabinet at 60° C., approx. 90 g of a colourless powder is obtained which, after comminution in a mixer, consists of particles of a diameter of from 200 to 3,000 μm. The powder can be graded by screening.

Thermal treatment of the cross-linked superabsorbent polymer

The dried superabsorbent polymer is maintained in a drying cabinet at 180° C. for approx. 15 minutes.

Measurement of the degree of swelling

Approx. 200 mg of the superabsorbent polymer is weighed into a 300 ml beaker. 200 ml of distilled water or 30 ml of a 0.9% solution of sodium chloride are poured over the polymer and the whole is left to stand at 200° C. When the equilibrium swelling state has been attained, the gel obtained is filtered through a filter cloth having a mesh size of 50 μm and finally weighed. The degree of swelling is then calculated from the ratio of the original weighing to the final weighing in g/g.

Each individual determination is carried out three times. The accuracy of measurement is ±5%.

Degree of swelling in water without subsequent thermal treatment: 370 g/g, after subsequent thermal treatment: 290 g/g.

EXAMPLES 2 to 8

The results of Examples 2 to 8 are summarised in Table 1. PAN (polyacrylonitrile) emulsions were used in the Examples in increasing order of degree of cross-linking. The superabsorbent polymers obtained after hydrolysis were separated into three grades of sizes by means of screening: <200 μm, 200 to 1,000 μm and 1,000 to 3,000 μm.

The degrees of swelling of the products in distilled water and in 0.9% NaCl solution are shown in the final two columns of the Table.

It can clearly be seen from this series of experiments that the capacity of the samples to absorb water decreases with increasing degree of cross-linking, both in distilled water and in 0.9% NaCl solution, while the gel strength increases (see Table 2).

TABLE 1

| Example No. | DVB [%] | sc of PAN emulsion [%] | ps of PAN emulsion [μm] | Hydrolysis temperature (°C.) | Duration of hydrolysis (h) | $[C_xPAN]$ % by weight | $[C_oNaOH]$ % by weight | Yield* (g) | Particle size [μm] | Degree of swelling (g/g) $H_2O$ | 0.9% NaCl |
|---|---|---|---|---|---|---|---|---|---|---|---|
| 2 | 0.25 | 20.9 | 120 | 95 | 2.0 | 11 | 4.15 | 92.0 | <200 | 670 ± 10 | 53.4 |
|   |      |      |     |    |     |    |      |      | 200–1,000 | 653 ± 8 | 52.0 |
|   |      |      |     |    |     |    |      |      | 1,000–3,000 | 630 ± 5 | 51.0 |
| 3 | 0.5 | 21.5 | 125 | 95 | 2.0 | 11 | 4.15 | 91.5 | <200 | 500 ± 20 | 46.1 |
|   |     |      |     |    |     |    |      |      | 200–1,000 | 490 ± 10 | 45.8 |
|   |     |      |     |    |     |    |      |      | 1,000–3,000 | 470 ± 5 | 44.9 |
| 4 | 0.75 | 21.1 | 129 | 95 | 2.0 | 11 | 4.15 | 91.0 | <200 | 400 ± 10 | 43.9 |
|   |      |      |     |    |     |    |      |      | 200–1,000 | 395 ± 15 | 43.0 |
|   |      |      |     |    |     |    |      |      | 1,000–3,000 | 350 ± 10 | 42.6 |
| 5 | 1.0 | 29.2 | 176 | 95 | 1.3 | 13.0 | 4.9 | 91.5 | <200 | 305 ± 5 | 41.5 |
|   |     |      |     |    |     |      |     |      | 200–1,000 | 280 ± 3 | 38.7 |
|   |     |      |     |    |     |      |     |      | 1,000–3,000 | 260 ± 6 | 37.3 |
| 6 | 1.0 | 29.2 | 176 | 95 | 1.0 | 14.0 | 4.91 | 90.9 | <200 | 205 ± 6 | 32.5 |
|   |     |      |     |    |     |      |      |      | 200–1,000 | 181 ± 7 | 32.4 |
|   |     |      |     |    |     |      |      |      | 1,000–3,000 | 192 ± 6 | 32.5 |
| 7 | 2.0 | 23.7 | 142 | 95 | 2.0 | 11.0 | 4.15 | 83.0 | <200 | 160 ± 1 | 32.3 |
|   |     |      |     |    |     |      |      |      | 200–1,000 | 155 ± 2 | 31.8 |
|   |     |      |     |    |     |      |      |      | 1,000–3,000 | 149 ± 1 | 30.1 |

DVB = divinylbenzene, sc = solids content, ps = particle size, *Yield in g relates to the use of 53 g of PAN, calculated as solid substance Degree of swelling in 0.9% sodium chloride solution without subsequent thermal treatment: 38.5 g/g, after subsequent thermal treatment: 32.3 g/g.

Measurement of the gel strength

Apparatus: Stevens L.F.R.A. Texture Analyzer

Principle of measurement: A cylindrical or conical test probe is pressed at a preselected velocity and distance into the gel test sample. The resulting force in grams is measured and digitally displayed.

Carrying out of the measurements: 1 g of the sample under investigation is swelled for a period of 1 hour in 170 ml of deionised water. The gel is then transferred into a 150 ml beaker and stirred with a spatula until homogeneous. After the sample has been tempered at 20° C., the measuring device is adjusted to a velocity of 1 mm/sec and a penetration distance of 10 mm, as well as to the "normal" test programme. The test probe used is the cylindrical test probe with the marking TA 3, which has a diameter of 1 inch. At least two measurements are made on each sample.

Table 2 shows the results of the measurements made of the gel strengths of some examples selected from Table 1 (Examples 2 to 4) using the Stevens Texture Analyzer.

TABLE 2

| Example No. | [%] of DVB in polymers | Gel strength (g) Prior to thermal treatment | After thermal 180° C. | 200° C. |
|---|---|---|---|---|
| 2 | 0.25 | 30 | 54 | 82 |
| 3 | 0.50 | 47 | 73 | — |
| 4 | 0.75 | 66 | 81 | 99 |

It can clearly be seen from Table 2 that the gel strength of the superabsorbent polymers increases with increasing degree of cross-linking. It is moreover clear that the gel strengths can be increased still further by a subsequent thermal treatment for a short period at 180° C. and 200° C., with values of up to 99 g being obtained (see Example 4).

We claim:

1. Method for the preparation of superabsorbent polymers, characterised in that fine-particled aqueous emulsions of cross-linked homopolymers and/or copolymers of acrylonitrile are partly hydrolysed by reaction with aqueous solutions of alkali hydroxides, the polymers are precipitated as powders by addition of organic solvents which are miscible with water, are separated out, dried and then optionally heated for a short period.

2. Method according to claim 1, wherein, in order to prepare the cross-linked homopolymers and/or copolymers of acrylonitrile, polyfunctional monomers are used in quantities of between 0.2 and 4.0% by weight, referred to the monofunctional monomers employed.

3. Method according to claim 1, wherein divinylbenzene is used as a polyfunctional monomer for the preparation of fine-particled aqueous emulsions of cross-linked homopolymers and/or copolymers of acrylonitrile.

4. Method according to claim 1, wherein divinylbenzene is used in quantities of between 0.5 and 1.0% by weight, referred to the monofunctional monomers employed.

5. Method according to claim 1, wherein the molar ratio of the nitrile groups of the polymer to the alkali hydroxides is from 1:1 to 1:0.1.

6. Method according to claim 1, wherein the reaction is carried out at from 50° to 100° C.

7. Method according to claim 1, wherein from 20 to 90 mol-% of the nitrile groups of the cross-linked acrylonitrile polymer are converted into carboxylate groups or amide groups.

8. Method according to claim 1, wherein organic solvents which are miscible with water are employed to precipitate the powders.

9. Method according to claim 1, wherein the precipitated powders are heated to 150° to 250° C. for 2 to 30 minutes.

10. The method of claim 1, wherein particles in the fine-particled aqueous emulsion have an average diameter of 100–300 nm.

* * * * *